United States Patent
Randhawa

(10) Patent No.: US 10,206,870 B2
(45) Date of Patent: Feb. 19, 2019

(54) TOPICAL COMPOSITION CONTAINING GLYCERIN AND YEAST EXTRACT

(71) Applicant: Johnson & Johnson Consumer Inc., Skillman, NJ (US)

(72) Inventor: Manpreet Randhawa, Robbinsville, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/799,350

(22) Filed: Oct. 31, 2017

(65) Prior Publication Data

US 2018/0161267 A1  Jun. 14, 2018

Related U.S. Application Data

(60) Provisional application No. 62/432,945, filed on Dec. 12, 2016.

(51) Int. Cl.
| | |
|---|---|
| *A61K 8/9728* | (2017.01) |
| *A61K 8/02* | (2006.01) |
| *A61K 8/34* | (2006.01) |
| *A61K 8/37* | (2006.01) |
| *A61K 8/49* | (2006.01) |
| *A61Q 19/08* | (2006.01) |
| *A61K 8/06* | (2006.01) |
| *A61Q 19/00* | (2006.01) |

(52) U.S. Cl.
CPC .......... *A61K 8/9728* (2017.08); *A61K 8/0216* (2013.01); *A61K 8/062* (2013.01); *A61K 8/345* (2013.01); *A61K 8/37* (2013.01); *A61K 8/4973* (2013.01); *A61Q 19/00* (2013.01); *A61Q 19/08* (2013.01); *A61K 2800/30* (2013.01)

(58) Field of Classification Search
None
See application file for complete search history.

(56) References Cited

U.S. PATENT DOCUMENTS

| 6,620,420 B2 | 9/2003 | Lanzendörfer et al. |
| 2007/0196523 A1 | 8/2007 | Koganov |

FOREIGN PATENT DOCUMENTS

| DE | 102009045753 A | 4/2011 |
| EP | 3165257 A | 5/2017 |
| EP | 3181142 A | 6/2017 |
| FR | 2897266 A | 8/2007 |
| FR | 2906719 A | 4/2008 |
| FR | 2938768 A | 5/2010 |
| FR | 2976490 A | 12/2012 |
| FR | 3016521 A | 7/2015 |

OTHER PUBLICATIONS

Ando et al., "Quasi-Drugs Developed in Japan for the Prevention or Treatment of Hyperpigmentary Disorders", *International Journal of Molecular Sciences* (2010) 11:2566-2575.
Handbook of Cosmetic Science and Technology, edited by A. Barel, M. Paye and H. Maibach, Chapter 35 "Skin Feel Agents" by G Zocchi, pp. 399-415, Published in 2001 by Marcel Dekker, Inc New York, NY.
Handbook of Cosmetic Science and Technology, edited by A. Barel, M. Paye and H. Maibach, Chapter 37 "Classification of surfactants" by Oldenhove de Guertechin, pp. 431-450, Published in 2001 by Marcel Dekker, Inc New York, NY.
Handbook of Non-Invasive Methods and the Skin, 2nd Edition, eds. J. Serup, G. Jemec & G. Grove, Chapter 66 "Suction Chamber Method for Measurement of Skin Mechanics: The Cutometer" by O'goshi (2006) pp. 579-582.
Solano et al., "Hypopigmenting agents: an updated review on biological, chemical and clinical aspects", *Pigment Cell Res.* (2006) 19:550-571.
Mintel Database GNPD [Online], "Anti-aging neck cream", Nov. 2011 (XP002777989).
Mintel Database GNPD [Online], "Gel cream", Nov. 2015 (XP002777990).
Mintel Database GNPD [Online], "Twinkle twinkle facial lotion", Feb. 2013 (XP002777991).
Anonymous, "Olivem 1000", Nov. 2, 2002, retrieved from the internet, URL:https://www.lotioncrafter.com/reference/Olivem_1000.pdf [retrieved on Feb. 6, 2011] (XP055448618).
European search report dated Feb. 20, 2018, for EP application 17206433.9.

*Primary Examiner* — Brian Gangle

(57) ABSTRACT

The present invention provides a topical composition comprising (a) 0.5 to 25 weight percent of glycerin; (b) 0.1 to 5 weight percent of cetearyl olivate; (c) 0.1 to 5 weight percent of sorbitan olivate; and (d) 0.01. to 1 weight percent of extract of *Pichia anomala*; wherein the composition is substantially free of fatty alcohols and is in the form of a gel cream.

4 Claims, No Drawings

TOPICAL COMPOSITION CONTAINING GLYCERIN AND YEAST EXTRACT

CROSS REFERENCE TO RELATED APPLICATIONS

This application claims priority of the benefits of U.S. Provisional Application Ser. No. 62/432,945 filed Dec. 12, 2017. The complete disclosure of the aforementioned U.S. patent application is hereby incorporated by reference for all purposes.

FIELD OF THE INVENTION

The present invention provides a topical composition comprising (a) 0.5 to 25 weight percent of glycerin; (b) 0.1 to 5 weight percent of cetearyl olivate; (c) 0.1 to 5 weight percent of sorbitan olivate; and (d) 0.01 to 1 weight percent of extract of *Pichia anomala*; wherein the composition is substantially free of fatty alcohols and is in the form of a gel cream.

BACKGROUND OF THE INVENTION

Gel creams are a desirable form of topical skin care compositions. The gel cream aesthetic is characterized with a watery break, semi-translucent aspect and light after-feel.

NEUTROGENA Hydro Boost Gel Cream, commercially available from Johnson & Johnson Consumer Inc., is a gel cream providing long lasting moisturization benefits. It absorbs into the skin quickly, like a gel, but has the long-lasting, intense moisturizing power of a cream. It contains hyaluronic acid along with glycerin, cetearyl olivate, and sorbitan olivate.

U.S. Pat. No. 6,620,420 discloses cosmetic or dermatological gel creams of the oil-in-water type, comprising: (i) up to 90% by weight of a water phase, (ii) up to 20% by weight of a lipid phase, based on the total weight of the preparations, (iii) up to 5% by weight of one or more emulsifiers, (iv) also comprising up to 5% by weight of one or more ammonium acrylolydimethyltaurate/vinylpyrrolidone copolymers (ARISTOFLEX® AVC commercially available from Clariant GmbH).

*Pichia* is a genus of yeasts in the family Saccharomycetaceae. More than 100 species of this genus are known. The most well-known species include *Pichia anomala, Pichia guilliermondii, Pichia norvegensis,* and *Pichia ohmeri.*

*Pichia anomala* (formerly named *Hansenula anomala*) can be found in raw milk and cheese. The extracts of yeasts of the genus *Pichia* are rich in mannans, polysaccharides composed of mannose monomers. *Pichia anomala* and mannans are known to be used in the treatment of aging skin. See, for example, FR 2938768, FR 2906719, FR 2897266 and FR 2976490.

PRO-LIPISKIN® is a commercially available cosmetic ingredient containing extract of *Pichia anomala*. It is produced by a *Pichia* strain isolated from sugar cane. It is available from Silab-France.

There exists a need for gel cream formulas with improved anti-aging benefits.

Applicant has now discovered that compositions containing glycerin and yeast extract increase the levels of glycosaminoglycans (GAGs) produced by skin in need or treatment for signs of skin aging when administered topically. In particular, these compositions contain glycerin, cetearyl olivate, sorbitan olivate, and extract of *Pichia anomala*, but are substantially free of fatty alcohols, particularly cetyl alcohol and behenyl alcohol.

Glycosaminoglycans (GAGs), such as hyaluronic acid and chondroitin sulfate, are predominantly synthesized by fibroblasts. It is known that the skin aging process brings about a decline in these metabolic activities, resulting in a decrease in the GAG's of the extracellular matrix of the dermis, and a decrease in cell growth, resulting in a detrimental change in the mechanical properties of the skin, in particular its firmness, elasticity, tonicity, and/or suppleness.

Applicant has found the compositions of the invention increase the amount of hyaluronic acid and chondroitin sulfate in skin topically treated with them.

SUMMARY OF THE INVENTION

The present invention provides a topical composition comprising (a) 0.5 to 25 weight percent of glycerin; (b) 0.1 to 5 weight percent of cetearyl olivate; (c) 0.1 to 5 weight percent of sorbitan olivate; and (d) 0.01 to 1 weight percent of extract of *Pichia anomala*; wherein the composition is substantially free of fatty alcohols and is in the form of a gel cream.

DETAILED DESCRIPTION

It is believed that one skilled in the art can, based on the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, percentages used to express amounts of ingredients are percentage by weight (i.e., % (W/W). Similarly weight ratios used to express relative proportions of ingredients are also determined using percentage by weight (i.e., weight ratios are calculated by dividing the percentage by weight of one ingredient by another). Unless stated otherwise, all ranges are inclusive of the endpoints, e.g., "from 4 to 9" includes the endpoints 4 and 9.

As used herein, a "product" is optionally in finished packaged form. In one embodiment, the package is a container such as a plastic, metal or glass tube or jar containing the composition. The product may further contain additional packaging such as a plastic or cardboard box for storing such container. In one embodiment, the product comprises a composition of the invention and contains instructions directing the user to apply the composition to the skin or hair.

As used herein, "topically applying" means directly laying on or spreading on outer skin, the scalp, or hair, e.g., by use of the hands or an applicator such as a wipe, roller, or spray.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically acceptable" means that the ingredients the term describes are suitable for use in contact with tissues (e.g., the skin or hair) without undue toxicity, incompatibility, instability, irritation, allergic response, or the like.

In certain embodiments, the compositions of the present invention are suitable for treating signs of skin aging. As used herein, "signs of skin aging" includes the presence of lines and wrinkles, loss of elasticity, uneven skin, and blotchiness. In a particularly preferred embodiment, the sign of aging is the presence of lines and wrinkles and/or loss of elasticity.

As used herein, "treating signs of skin aging" refers to mitigating, reducing, preventing, improving, or eliminating the presence or signs of skin aging described above.

As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

As used herein, "improving the firmness of skin" means the enhancing of the firmness or elasticity of the skin, preventing the loss of firmness or elasticity of skin, or preventing or treating sagging, lax and loose skin. The firmness or elasticity of the skin can be measured by use of a cutometer. See *Handbook Of Non-Invasive Methods And The Skin*, eds. J. Serup, G. Jemec & G. Grove, Chapter 66.1 (2006). The loss of skin elasticity or firmness may be a result of a number of factors, including but not limited to aging, environmental damage, or the result of an application of a cosmetic to the skin.

As used herein, "improving the texture of skin" means the smoothing of the surface of the skin to remove either bumps or crevasses on the skin surface.

As used herein, "improving the appearance of wrinkles in skin" means preventing, retarding, arresting, or reversing the process of wrinkle and fine line formation in skin.

As used herein, the term "safe and effective amount" means an amount sufficient to induce the desired effect, but low enough to avoid serious side effects. The safe and effective amount of the compound, extract, or composition will vary with, e.g., the age, health and environmental exposure of the end user, the duration and nature of the treatment, the specific extract, ingredient, or composition employed, the particular carrier utilized, and like factors.

As used herein, the term "gel cream" means a formulation with low levels of oil droplets suspended in aquous gel matrix.

In certain embodiments, the compositions of the present invention are suitable for treating skin in need of improving skin barrier function and moisturization. As used herein, "skin in need of improving skin barrier function and moisturization" means skin that is, but not limited to, lacking in moisture, lacking in sebum, cracked, dry, itchy, scaly, xerodermic, dehydrated, lacks suppleness, lacks radiance, dull, or lacks lipids.

As described herein, applicants have discovered provides a topical composition comprising (a) 0.5 to 25 weight percent of glycerin; (b) 0.1 to 5 weight percent of cetearyl olivate; (c) 0.1 to 5 weight percent of sorbitan olivate; and (d) 0.01 to 1weight percent of extract of *Pichia anomala*; wherein the composition is substantially free of fatty alcohols and is in the form of a gel cream.

Glycerin

The composition comprises 0.5 to 25 weight percent glycerin. In one embodiment, the composition comprises 1 to 6 weight percent glycerin.

Cetearyl Olivate and Sorbitan Olivate

The composition comprises 0.1 to 5 weight percent of cetearyl olivate. In one embodiment, the composition comprises 0.1 to 2 weight percent of cetearyl olivate.

The composition also comprises 0.1 to 5 weight percent of sorbitan olivate. In one embodiment, the composition comprises 0.1 to 2 weight percent of sorbitan olivate.

A convenient source of cetearyl olivate and sorbitan olivate is Olivem® 1000, commercially available from Hallstar itali.

Yeast Extract

The topical composition comprises one or more extracts of *Pichia anomala*. *Pichia* is a genus of yeasts in the family Saccharomycetaceae. More than 100 species of this genus are known. The most well-known species include *Pichia anomala*, *Pichia guilliermondii*, *Pichia norvegensis*, and *Pichia ohmeri*. *Pichia anomala* (formerly named *Hansenula anomala*) can be found in raw milk and cheese. The extracts of yeasts of the genus *Pichia* are rich in mannans, polysaccharides composed of mannose monomers. *Pichia anomala* and mannans are known to be used in the treatment of aging skin. See, for example, FR 2938768, FR 2906719, FR 2897266 and FR 2976490.

In particular, such extracts may be extracts produced using one of the various strains of *Pichia anomala* isolated from the fruit or other aerial parts of a plant. Any cosmetically acceptable extract of *Pichia anomala* may be used.

One example of a suitable extract of *Pichia anomala* is PRO-LIPISKIN, commercially available from Silab-France. It is produced from a strain of *Pichia anomala* present on sugar cane.

Another example of a suitable extract of *Pichia anomala* is produced from a strain of *Pichia anomala* present on fruit or leaves of a kiwi plant.

Both of the foregoing may be provided as aqueous solutions containing dry matter in the range of about 20%, more specifically 2 to 10%, most specifically 3 to 7%. Accordingly, the composition may contain 0.01. to 1 weight percent of extract of *Pichia anomala*.

PRO-LIPISKIN® is a commercially available cosmetic ingredient containing extract of *Pichia anomala*. It is produced by *Pichia* strain isolated from sugar cane. It is available from Silab-France.

In one embodiment, the composition is substantially free of fatty alcohols. In particular, the composition is substantially free of cetyl alcohol and behenyl alcohol. As used herein, the phrase "substantially free" means containing less than 0.1 weight percent, or less than 0.01 weight percent, or none of an ingredient. In one embodiment of the invention, the composition contains no cetyl alcohol or behenyl alcohol. In another embodiment of the invention, the composition contains no fatty alcohols.

In another embodiment, the composition has a pH of less than 7.

Additional Cosmetically Active Agents

The compositions of the present invention may further comprise any of a variety of additional cosmetically active agents. Examples of suitable additional active agents include: skin lightening agents, darkening agents, additional anti-aging agents, tropoelastin promoters, collagen promoters, anti-acne agents, shine control agents, antimicrobial agents such as anti-yeast agents, anti-fungal, and anti-bacterial agents, anti-inflammatory agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, hair growth enhancing agents, hair growth delaying agents, firming agents, hydration boosters, efficacy boosters, anti-callous agents, agents for skin conditioning, anti-cellulite agents, odor-control agents such as odor masking or pH-changing agents, and the like.

Examples of various suitable additional cosmetically acceptable actives include hydroxy acids; benzoyl peroxide; D-panthenol; UV filters such as but not limited to avobenzone (PARSOL 1789), bisdisulizole disodium (NEO HELIOPAN AP), diethylamino hydroxybenzoyl hexyl benzoate (UVINUL A Plus), ecamsule (MEXORYL SX), methyl anthranilate, 4-aminobenzoic acid (PABA), cinoxate, ethylhexyl triazone (UVINUL T 150), homosalate, 4-methylbenzylidene camphor (PARSOL 5000), octyl methoxycinnamate (Octinoxate), octyl salicylate (Octisalate), padimate 0 (ESCALOL 507), phenylbenzimidazole sulfonic acid (ENSULIZOLE), polysilicone-15 (PARSOL SLX), trolamine salicylate, Bemotrizinol (TINOSORB S), benzophenones 1-12, dioxybenzone, drometrizole trisiloxane (MEXORYL XL), iscotrizinol (UVASORB HEB), octocrylene, oxybenzone (EUSOLEX 4360), sulisobenzone, bisoctrizole (TINOSORB M), titanium dioxide, zinc oxide; carotenoids; free radical scavengers; spin traps; retinoids and retinoid precursors such as retinol, retinoic acid and retinyl palmitate; ceramides; polyunsaturated fatty acids; essential fatty acids; enzymes; enzyme inhibitors; minerals; hormones such as estrogens; steroids such as hydrocortisone; 2-dimethylaminoethanol; copper salts such as copper chloride; peptides containing copper, coenzyme Q10; amino acids such a proline; vitamins; lactobionic acid; acetyl-coenzyme A; niacin; riboflavin; thiamin; ribose; electron transporters such as NADH and FADH2; and other botanical extracts such as oat, aloe vera, Feverfew, Soy, Shiitake mushroom extracts, and derivatives and mixtures thereof.

In certain preferred embodiments, the composition comprises at least one additional skin moisturizing active agent.

In certain preferred embodiments, the composition comprises at least one additional agent for improving the appearance of at least one sign of aging in skin. Examples of suitable additional agents improving the appearance of at least one sign of aging in skin include, but are not limited to, tropoelastin promoters, collagen promoters, retinoids, dimethylaminoethanol, N,N,N',N'-tetrakis(2-hydroxypropyl) ethylenediamine, alpha hydroxy acids, polyhydroxyacids, and combinations of two or more thereof.

"Tropoelastin promoters," as used herein, refers to a class of compounds that possess the biological activity of enhancing the production of tropoelastin. Tropoelastin promoters, according to the present invention, include all natural or synthetic compounds that are capable of enhancing the production of tropoelastin in the human body.

Examples of suitable tropoelastin promoters include, but are not limited to, blackberry extracts, cotinus extracts, feverfew extracts, and bimetal complexes having copper and/or zinc constituents. The bimetal complex having copper and/or zinc constituents may be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof. In a preferred embodiment, the tropoelastin promoter is selected from blackberry extracts, cotinus extracts, feverfew extracts, and combinations thereof. In a particularly preferred embodiment, the tropoelastin promoter is selected from blackberry extracts, feverfew extracts, and combinations thereof.

By "blackberry extract," it is meant a blend of compounds isolated from the plant of the genus *Rubus*, and preferably *Rubus fruticosus*. In one embodiment, the compounds are isolated from the flowers of the plant. In a further embodiment, the compounds are isolated from dried flowers of the plant. Such compounds may be isolated from one or more part of the plant (e.g., the whole plant, flower, seed, root, rhizome, stem, fruit and/or leaf of the plant). In a preferred embodiment, the blackberry extract is a blackberry leaf extract. One particularly suitable blackberry extract is produced by extracting the leaves of *Rubus fruticosus* with a mixture of water and ethanol compounded to an activity of about 5% to about 10%, with a maltodextrin matrix, commercially available from Symrise Inc. of Teterboro, N.J., and is sold under the name SYMMATRIX.

Compositions of the present invention may include a cosmetically effective amount of one or more tropoelastin promoters such as those described above. The compositions preferably include, on an active basis, from about 0.1% to about 10% of the tropoelastin promoters, more preferably from about 0.5% to about 5% of tropoelastin promoters, and most preferably from about 0.5% to about 2% of the tropoelastin promoters.

"Collagen promoter," as used herein, refers to compounds that possess the biological activity of enhancing the production of collagen. "Non-retinoid collagen promoters" according to the present invention include all natural or synthetic compounds that are not retinoids, or derived from retinoids, and are capable of enhancing the production of collagen in the human body.

Examples of suitable collagen promoters include, but are not limited to the following: Retinoids including retinol, retinaldehyde, and retinoic acid, extracts of feverfew (*Tanacetum parthenium*), extracts of *Centella asiatica*, and extracts of *Siegesbeckia orientalis*; extracts of soy; collagen-promoting peptides; ursolic acid; and asiaticoside.

*Centella asiatica*, also known as *Violette marronne* on Reunion Island, Gotu Kola or Indian pennywort in India, *Centella repanda* in North America, and Talapetraka in Madagascar, is a polymorphous herb and belongs to the family of Umbelhferae (Apiaceae), particularly to the Hydrocotyle subfamily. It grows wild throughout the tropics and prefers moist and shady regions at an altitude of about 600 to 1200 meters above sea level. *Centella asiatica* has three varieties: Typica, Abyssinica, and Floridana. The herb is known and used for its healing, sedative, analgesic, antidepressant, antiviral and antimicrobial properties. The biological activity of the herb appears to be due to the presence of triterpene molecules in the herb. A suitable extract of *Centella asiatica* is available as TECA from Bayer Consumer HealthCare of Basel, Switzerland.

By "extracts of *Siegesbeckia orientalis*," is meant any of various extracts of the plant *Siegesbeckia orientalis*, including Darutoside available from Sederma (Croda International Group of Edison, N.J.).

Suitable collagen-promoting peptides include the following matrikine peptides, (i.e., a peptide derived from the degradation of extracellular matrix proteins—collagen, elastin, or proteoglycan) including palmitoyl pentapeptides, such as MATRIXYL from Sederma (Croda International Group of Edison, N.J.); GHK copper peptide available as PROCYTE from Photomedex of Montgomeryville, Pa.; Palmitoyl GHK peptide available as Biopoeptide CL from Sederma (Croda International Group of Edison, N.J.); Biomimetic tetrapeptides, such as those available as Chronoline Tri Peptide from Unipex of Québec, Canada; and Palmitoyl tri-peptide, available as Syn-Coll from DSM of Basel, Switzerland.

Ursolic acid is also known as pentacyclic triterpene acid, Prunol, Malol, Urson, beta-ursolic acid and 3-Beta-Hydroxy-Urs-12-En-28-Oic Acid. It is commercially available for example from Sigma-Aldrich of St. Louis, Mo.

Asiaticoside, also known chemically as: [6-[[3,4-dihydroxy-6-(hydroxynnethyl)-5-(3,4,5-trihydroxy-6-methyloxan-2-yl)oxyoxan-2-yl]oxymethyl]-3,4,5-trihydroxyoxan-2-yl]10,11-dihydroxy-9-(hydroxynnethyl)-1,2,6a,6b,9,12a-hexamethyl-2,3,4,5,6,6a,7,8,8a,10,11,12,13,14b-tetradecahydro-1H-picene-4a-carboxylate) is commercially available for example from Bayer Santé Familiale Division Serdex, 69, Boulevard Victor Hugo 93400 SAINT-OUEN France.

Compositions of the present invention may include a cosmetically effective amount of one or more collagen promoters. The compositions preferably include, on an active basis, from about 0.1% to about 10% of the collagen promoters, more preferably from about 0.5% to about 5% of collagen promoters, and most preferably from about 0.5% to about 2% of the collagen promoters.

The compositions of the present invention may comprise additionally at least one skin lightening active agent. Examples of suitable skin lightening active agents include, but are not limited to, tyrosinase inhibitors, melanin-degradation agents, melanosome transfer inhibiting agents including PAR-2 antagonists, exfoliants, sunscreens, retinoids, antioxidants, Tranexamic acid, tranexamic acid cetyl ester hydrochloride, skin bleaching agents, linoleic acid, adenosine monophosphate disodium salt, Chamomilla extract, allantoin, opacifiers, talcs and silicas, zinc salts, and the like, and other agents as described in Solano et al. Pigment Cell Res. 19 (550-571) and Ando et al. Int J Mol Sci 11 (2566-2575).

Examples of suitable tyrosinase inhibitors include but, are not limited to, Vitamin C and its derivatives, Vitamin E and its derivatives, Kojic Acid, Arbutin, resorcinols, hydroquinone, Flavones e.g. Licorice flavanoids, Licorice root extract, Mulberry root extract, *Dioscorea Coposita* root extract, Saxifraga extract and the like, Ellagic acid, Salicylates and derivatives, Glucosamine and derivatives, Fullerene, Hinokitiol, Dioic acid, Acetyl glucosamine, 5,5'-dipropyl-biphenyl-2,2'-diol (Magnolignan), 4-(4-hydroxyphenyl)-2-butanol (4-HPB), combinations of two or more thereof, and the like. Examples of vitamin C derivatives include, but are not limited to, ascorbic acid and salts, Ascorbic Acid-2-Glucoside, sodium ascorbyl phosphate, magnesium ascorbyl phosphate, and natural extract enriched in vitamin C. Examples of vitamin E derivatives include, but are not limited to, alpha-tocopherol, beta, tocopherol, gamma-tocopherol, delta-tocopherol, alpha-tocotrienol, beta-tocotrienol, gamma-tocotrienol, delta-tocotrienol and mixtures thereof, tocopherol acetate, tocopherol phosphate and natural extracts enriched in vitamin E derivatives. Examples of resorcinol derivatives include, but are not limited to, resorcinol, 4-substituted resorcinols like 4-alkylresorcinols such as 4-butyresorcinol (rucinol), 4-hexylresorcinol (Synovea HR, Sytheon), phenylethyl resorcinol (Symwhite, Symrise), 1-(2,4-dihydroxyphenyl)-3-(2,4-dimethoxy-3-methylphenyl)-Propane (nivitol, Unigen) and the like and natural extracts enriched in resorcinols. Examples of salicylates include, but are not limited to, 4-methoxy potassium salicylate, salicylic acid, acetylsalicylic acid, 4-methoxysalicylic acid and their salts. In certain preferred embodiments, the tyrosinase inhibitors include a 4-substituted resorcinol, a vitamin C derivative, or a vitamin E derivative. In more preferred embodiments, the tyrosinase inhibitor comprises Phenylethyl resorcinol, 4-hexyl resorcinol, or ascorbyl-2-glucoside.

Examples of suitable melanin-degradation agents include, but are not limited to, peroxides and enzymes such as peroxidases and ligninases. In certain preferred embodiments, the melanin-inhibiting agents include a peroxide or a ligninase.

Examples of suitable melanosome transfer inhibiting agents include PAR-2 antagonists such as soy trypsin inhibitor or Bowman-Birk Inhibitor, Vitamin B3 and derivatives such as Niacinamide, Essential soy, Whole Soy, Soy extract. In certain preferred embodiments, the melanosome transfer inhibiting agents includes a soy extract or niacinamide.

Examples of exfoliants include, but are not limited to, alpha-hydroxy acids such as lactic acid, glycolic acid, malic acid, tartaric acid, citric acid, or any combination of any of the foregoing, beta-hydroxy acids such as salicylic acid, polyhydroxy acids such as lactobionic acid and gluconic acid, and mechanical exfoliation such as microdermabrasion. In certain preferred embodiments, the exfoliants include glycolic acid or salicylic acid.

Examples of retinoids include, but are not limited to, retinol (Vitamin A alcohol), retinal (Vitamin A aldehyde), retinyl acetate, retinyl propionate, retinyl linoleate, retinoic acid, retinyl palmitate, isotretinoin, tazarotene, bexarotene, Adapalene, combinations of two or more thereof and the like. In certain preferred embodiments, the retinoid is selected from the group consisting of retinol, retinal, retinyl acetate, retinyl propionate, retinyl linoleate, and combinations of two or more thereof. In certain more preferred embodiments, the retinoid is retinol.

Examples of antioxidants include, but are not limited to, water-soluble antioxidants such as sulfhydryl compounds and their derivatives (e.g., sodium metabisulfite and N-acetyl-cysteine, glutathione), lipoic acid and dihydrolipoic acid, stilbenoids such as resveratrol and derivatives, lactoferrin, iron and copper chelators and ascorbic acid and ascorbic acid derivatives (e.g., ascobyl-2-glucoside, ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinones. Natural extracts containing antioxidants suitable for use in the compositions of this invention, include, but not limited to, extracts containing flavonoids and isoflavonoids and their derivatives (e.g., genistein and diadzein), extracts containing resveratrol and the like.

Examples of such natural extracts include grape seed, green tea, black tea, white tea, pine bark, feverfew, parthenolide-free feverfew, oat extracts, blackberry extract, cotinus extract, soy extract, pomelo extract, wheat germ extract, Hesperedin, Grape extract, Portulaca extract, Licochalcone, chalcone, 2,2'-dihydroxy chalcone, Primula extract, propolis, and the like.

Compositions of the present invention may include a cosmetically effective amount of one or more anti-inflammatory compounds.

Examples of suitable anti-inflammatory agents include substituted resorcinols, (E)-3-(4-methylphenylsulfonyl)-2-propenenitrile (such as "Bay 11-7082," commercially available from Sigma-Aldrich of St. Louis, Mo.), tetrahydrocurcuminoids (such as Tetrahydrocurcuminoid CG, available from Sabinsa Corporation of Piscataway, N.J.), extracts and materials derived from the following: *Phellodendron amurense* Cortex Extract (PCE), Non-Denatured Soy (*Glycine max*), Feverfew (*Tanacetum parthenium*), Ginger (*Zingiber officinale*), Ginko (*Ginkgo biloba*), Madecassoside (*Centella asiatica* extract ingredient), Cotinus (*Cotinus coggygria*), Butterbur Extract (*Petasites hybridus*), Goji Berry (*Lycium barbarum*), Milk Thistle Extract (*Silybum marianum*), Honeysuckle (*Lonicera japonica*), Basalm of Peru (*Myroxylon pereirae*), Sage (*Salvia officinalis*), Cranberry Extract (*Vaccinium oxycoccos*), Amaranth Oil (*Amaranthus cruentus*), Pomegranate (*Punica granatum*), Yerbe Mate (*Ilex paraguariensis* Leaf Extract), White Lily Flower Extract (*Lilium candidum*), Olive Leaf Extract (*Olea europaea*), Phloretin (apple extract), Oat Flour (*Aveena sativa*), Lifenol (Hops: *Humulus lupulus*) Extract, Bugrane P (*Ononis spinosa*), Licochalcone (Licorice: *Glycyrrhiza* inflate extract ingredient), Symrelief (Bisabolol and Ginger extract), combinations of two or more thereof, and the like.

In one embodiment, the anti-inflammatory agent is a resorcinol. Particularly suitable substituted resorcinols include 4-hexyl resorcinol and 4-octylresorcinol, particularly 4-hexyl resorcinol. 4-Hexyl resorcinol is commercially available as SYNOVEA HR from Sytheon of Lincoln Park, N.J. 4-Octylresorcinol is commercially available from City Chemical LLC of West Haven, Conn.

By "extracts of feverfew," it is meant extracts of the plant "*Tanacetum parthenium*," such as may be produced according to the details set for the in US Patent Application Publication No. 2007/0196523, entitled "PARTHENOLIDE FREE BIOACTIVE INGREDIENTS FROM FEVERFEW (*TANACETUM PARTHENIUM*) AND PROCESSES FOR THEIR PRODUCTION." One particularly suitable feverfew extract is commercially available as about 20% active feverfew, from Integrated Botanical Technologies of Ossining, N.Y.

In one embodiment, the topical composition comprises hyaluronic acid. The hyaluronic acid may be linear, cross-linked, or a mixture of linear and cross-linked hyaluronic acid. It may be in a salt form, such as sodium hyaluronate. The molecular weight of the hyaluronic acid may vary as desired from very low molecular weight to very high molecular weight.

A commercially available cross-linked hyaluronic acid useful in the present invention is HyaCare® Filler CL from Evonik Industries AG. HyaCare® Filler CL is a fermentation-derived high-quality biopolysaccharide of high purity which is obtained by a solvent-free process. It is skin-identical hyaluronic acid with a medium molecular weight of 700 kDa.

Another commercially available cross-linked hyaluronic acid useful in the present invention is Hylasome® EG10, sold by Vantage Specialty Ingredients.

The cross-linked hyaluronic acid may be prepared as known in the art. For example, natural or synthetic sources of linear hyaluronic acid may be cross-linked with a variety of cross-linkers, including divinyl sulfone (DVS), formaldehyde, polyanhydrides, polyaldehydes, polyhydric alcohols, carbodiimides, epichlorohydrin, ethylene glycol diglycidylether, butanediol diglycidylether, polyglycerol polyglycidylether, polyethylene glycol, polypropylene glycol diglycidylether, bis- or poly-epoxy cross-linkers such as 1,2,3,4-diepoxybutane or 1,2,7,8-diepoxyoctane, or other cross-linkers known in the art. The degree of cross-linking may be adjusted also as known in the art. In another embodiment, the composition comprises a citrus fruit extract, for example a lemon peel extract.

Other Ingredients

The compositions of the present invention are applied topically to human skin or hair. Accordingly, the composition may further include cosmetically acceptable topical ingredients as known in the personal care art for use with gel cream formulations of the oil-in-water emulsion type.

In certain preferred embodiments, the composition comprises one or more topical ingredients selected from the group consisting of: surfactants, chelating agents, additional emollients, humectants, conditioners, preservatives, opacifiers, fragrances and the like.

Additional emollients include compounds that help to maintain the soft, smooth, and pliable appearance of the skin (e.g., by remaining on the skin surface or in the stratum corneum to act as a lubricant). Examples of suitable emollients include those found in Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.), and include, but are not limited to, petrolatum, hexyldecyl stearate and plant, nut, and vegetable oils such as macadamia nut oil, rice bran oil, grape seed oil, palm oil, prim rose oil, hydrogenates peanut oil, and avocado oil.

What is meant by a humectant is a compound intended to increase the water content of the top layers of skin (e.g., hygroscopic compounds). Examples of suitable humectants include those found Chapter 35, pages 399-415 (Skin Feel Agents, by G Zocchi) in Handbook of Cosmetic Science and Technology (edited by A. Barel, M. Paye and H. Maibach, Published in 2001 by Marcel Dekker, Inc New York, N.Y.) and include, but are not limited to, glycerin, sorbitol or trehalose (e.g., α,α-trehalose, β,β-trehalose, α,β-trehalose) or a salt or ester thereof (e.g., trehalose 6-phosphate).

What is meant by a surfactant is a surface-active agent intended to cleanse or emulsify. Examples of suitable surfactants include those found in Chapter 37, pages 431-450 (Classification of surfactants, by L. Oldenhove de Guertechin) in Handbook of Cosmetic Science and Technology (edited by A. Barel, M. Paye and H. Maibach, Published in 2001 by Marcel Dekker, Inc New York, N.Y.) and include, but are not limited to anionic surfactants such as sulfates, cationic surfactants such as betaines, amphoteric surfactants such as sodium coco glycinate, noionic surfactants such as alkyl polyglucosides.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the trade name VERSENE 100XL.

Suitable preservatives include, for example, parabens, quaternary ammonium species, phenoxyethanol, benzoates, DMDM hydantoin, organic acids and are present in the composition in an amount, based upon the total weight of the composition, from about 0 to about 1 percent or from about 0.05 percent to about 0.5 percent.

Any of a variety of conditioners that impart additional attributes, such as gloss to the hair, are suitable for use in this invention. Examples include, but are not limited to, volatile silicone conditioning agent having an atmospheric pressure boiling point less than about 220° C. Examples of suitable volatile silicones nonexclusively include polydimethylsiloxane, polydimethylcyclosiloxane, hexamethyldisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids. Other suitable conditioners include cationic polymers, including polyquarterniums, cationic guar, and the like.

Any of a variety of commercially available pearlescent or opacifying agents are suitable for use in the composition. Examples of suitable pearlescent or opacifying agents include, but are not limited to, mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: $HO-(JO)_a-H$, wherein J is an alkylene group having from about 2 to about 3 carbon atoms; and a is 2 or 3; fatty alcohols containing from about 16 to about 22 carbon atoms; fatty esters of the formula: $KCOOCH_2L$, wherein K and L independently contain from about 15 to about 21 carbon atoms; inorganic solids insoluble in the shampoo composition, and mixtures thereof.

Any fragrance compositions suitable for use on skin may be used in accord with the present invention.

The composition may comprise a thickener such as hydroxyethyl acrylate/sodium acryloyldimethyl taurate copolymer. Such an ingredient is commercially available as Sepimax® C from Seppic. In one embodiment, the composition comprises about 0.1 to about 10, or about 1 to about 8, weight % thickener.

The amount and selection of the thickener allows for stabilization of the gel cream while maintain gel cream aesthetic and skin feel.

The composition may contain for example suitable gelling agents such as natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The additional cosmetically active agent may be present in a composition in any suitable amount, for example, in an amount of from about 0.0001% to about 20% by weight of the composition, e.g., about 0.001% to about 10% such as about 0.01% to about 5%. In certain preferred embodiments, in an amount of 0.1% to 5% and in other preferred embodiments from 1% to 2%.

The composition, and formulations and products containing such composition, may be prepared using methodology that is well known by an artisan of ordinary skill.

In one embodiment, the composition comprises dimethicone, carbomers, glycerin, beeswax, polyacrylamide, laureth-7, C13-14 isoparaffin, water, chlorphenesin, ethylhexylglycerin, phenoxyethanol, cetearyl olivate, sorbitan olivate, dimethicone, dimethicone crosspolymer, sodium hydroxide, dimethiconol, vinyl dimethicone crosspolymer, C12-14 pareth-12, sodium hyaluronate, and extract of *Pichia anomala*.

Methods

The present invention further comprises a method of improving the barrier function and moisturization of skin by applying to skin in need of improving skin barrier function and moisturization the composition of the invention. The method comprises for example topically applying the composition to skin in in need of improving skin barrier function and moisturization. Such topical application may be to any skin in need of treatment on the body, for example skin of the face, lips, neck, chest, back, arms, axilla, hands, feet and/or legs.

The present invention further comprises a method of improving the appearance of at least one sign of skin aging by applying to skin in need of improving the appearance of at least one sign of skin aging the composition of the invention. The method comprises for example topically applying the composition to skin in need of treatment of at least one sign of skin aging. Such topical application may be to any skin in need of treatment on the body, for example skin of the face, lips, neck, chest, back, arms, axilla, hands, feet and/or legs.

Any suitable method of applying the composition to the skin in need may be used. For example, the composition may be applied directly from a package to the skin in need, by hand to the skin in need, or may be transferred from a substrate such as a wipe or mask, or a combination of two or more thereof. In other embodiments, the composition may be applied via a dropper, tube, roller, spray, and patch or added to a bath or otherwise to water to be applied to the skin, and the like. The composition may be applied in a variety of manners/forms, including, without limitation, as a leave-on cream, mask, and/or serum.

The following non-limiting examples further illustrate the present invention.

Example 1

A topical gel cream composition according to the invention was made having the following ingredients.

TABLE 1

| INCI US | Primary FUNCTION | Weight % |
|---|---|---|
| Dimethicone | EMOLLIENT | 3.5 |
| Carbomer | VISCOSITY INCREASING | 0.15 |
| Glycerin | HUMECTANT | 6 |
| Synthetic Beeswax | FILM FORMING AGENT | 0.5 |
| Polyacrylamide; Laureth-7; C13-14 Isoparaffin | VISCOSITY INCREASING | 2 |
| Water | SOLVENT | 75.23 |
| Chlorphenesin | PRESERVATIVE | 0.2 |
| Ethylhexylglycerin; Phenoxyethanol | PRESERVATIVE | 0.8 |
| Cetearyl Olivate; Sorbitan Olivate | EMULSIFIER | 2 |
| Dimethicone; Dimethicone Crosspolymer | SKIN CONDITIONER | 1.5 |
| Sodium Hydroxide | PH ADJUSTER | 0.02 |
| Dimethicone; Dimethiconol | | 2 |

TABLE 1-continued

| INCI US | Primary FUNCTION | Weight % |
|---|---|---|
| Dimethicone/Vinyl Dimethicone Crosspolymer; C12-14 Pareth-12 | | 1 |
| Sodium Hyaluronate | SKIN CONDITIONER | 0.1 |
| Aq. Solution of extract of *Pichia anomala* | | 5 |

Example 2

A topical gel cream composition according to the invention was made having the following ingredients.

TABLE 2

| INCI US | Primary FUNCTION | Weight % |
|---|---|---|
| Dimethicone | EMOLLIENT | 3 |
| Glycerin | HUMECTANT | 5 |
| Steareth-10 | EMULSIFIER | 0.5 |
| Sclerotium Gum | VISCOSITY CONTROLLER | 0.4 |
| Water | SOLVENT | 77.4 |
| Chlorphenesin | PRESERVATIVE | 0.2 |
| Ethylhexylglycerin; Phenoxyethanol | PRESERVATIVE | 0.8 |
| Cetearyl Olivate; Sorbitan Olivate | EMULSIFIER | 1.5 |

TABLE 2-continued

| INCI US | Primary FUNCTION | Weight % |
|---|---|---|
| Dimethicone; Dimethicone Crosspolymer | SKIN CONDITIONER | 2.5 |
| Dimethicone; Dimethiconol | | 2 |
| Glyceryl Dilaurate | EMOLLIENT | 0.5 |
| Hydroxyethyl Acrylate/Sodium Acryloyldimethyl Taurate Copolymer | | 1.2 |
| Aq. Solution of extract of *Pichia anomala* | | 5 |

The invention claimed is:

1. A topical composition comprising:
 (a) 0.5 to 25 weight percent of glycerin;
 (b) 0.1 to 5 weight percent of cetearyl olivate;
 (c) 0.1 to 5 weight percent of sorbitan olivate; and
 (d) 0.01 to 1 weight percent of extract of *Pichia anomala*;
 wherein the composition is substantially free of fatty alcohols and is in the form of a gel cream.

2. The composition of claim 1 having a pH of less than about 7.

3. The composition of claim 1, wherein the extract of *Pichia anomala* is prepared from a strain of *Pichia anomala* present on sugar cane.

4. The composition of claim 1 substantially free of cetyl alcohol and behenyl alcohol.

* * * * *